United States Patent [19]

Forster

[11] Patent Number: 4,579,751

[45] Date of Patent: Apr. 1, 1986

[54] METHOD OF PRODUCING CONSTITUENT MATERIALS FOR GAS SENSORS

[75] Inventor: Martin Forster, Jona, Switzerland

[73] Assignee: Cerberus AG, Männedorf, Switzerland

[21] Appl. No.: 633,652

[22] Filed: Jul. 23, 1984

[30] Foreign Application Priority Data

Aug. 30, 1983 [CH] Switzerland ............ 4738/83

[51] Int. Cl.$^4$ ............................ B05D 3/06
[52] U.S. Cl. .................... 427/54.1; 338/34; 427/217
[58] Field of Search ............ 427/53.1, 54.1, 217; 338/34

[56] References Cited

U.S. PATENT DOCUMENTS

| | | |
|---|---|---|
| 3,644,795 | 2/1972 | Taguchi . |
| 4,001,757 | 1/1977 | Sato et al. . |
| 4,259,292 | 3/1981 | Ichinose et al. ............ 338/34 |
| 4,260,978 | 4/1981 | Yasuda et al. ............ 338/34 |
| 4,264,421 | 4/1981 | Bard et al. . |
| 4,286,378 | 9/1981 | Micheli . |
| 4,362,765 | 12/1982 | Abe et al. . |
| 4,407,865 | 10/1983 | Nice ............................ 427/217 |
| 4,484,992 | 11/1984 | Bühler et al. ............ 427/54.1 |

FOREIGN PATENT DOCUMENTS

| | | |
|---|---|---|
| 0005481 | 11/1979 | European Pat. Off. . |
| 2428488 | 1/1975 | Fed. Rep. of Germany . |
| 3245117 | 6/1983 | Fed. Rep. of Germany . |
| 2073827 | 10/1971 | France . |

*Primary Examiner*—John H. Newsome
*Attorney, Agent, or Firm*—Werner W. Kleeman

[57] ABSTRACT

Novel constituent materials for gas sensors detecting gaseous impurities in air contain metal oxides and catalyst additives. The materials are prepared by mixing a colloidal solution A of an oxide or a hydroxide of at least one metal selected from the groups Ib, IIa, IIb, IIIa, IIIb, IVa, IVb, Va, Vb, VIa, VIb, VIIb, VIII and the lanthanides and actinides of the periodic system with a solution B containing a salt or a complex compound of at least one metal selected from the group: lanthanum, chromium, manganese, iron, cobalt, nickel, copper, ruthenium, iridium, palladium, platinum, rhodium, osmium, silver, gold, antimony, bismuth, thorium, and irradiating the mixture thus obtained with light of the visible and ultraviolet spectral region in order to photochemically deposit the metal in finely distributed form on the metal oxide or metal hydroxide, respectively. The irradiated solution C thus obtained is processed without substantial change in the size of the colloidal particles of the metal oxide or metal hydroxide, respectively, in order to yield a solid D which subsequently is dried at a temperature which is higher than the intended operating temperature of the gas sensor by a maximum of 700° C., particularly by a maximum of 500° C. and preferably by a maximum of 300° C.

55 Claims, No Drawings

METHOD OF PRODUCING CONSTITUENT MATERIALS FOR GAS SENSORS

CROSS-REFERENCES TO RELATED APPLICATIONS

This application is related to (i) the commonly assigned, copending U.S. application Ser. No. 06/586,329, filed Mar. 5, 1984, entitled "DEVICE FOR THE DETECTION OF GASEOUS IMPURITIES IN AIR BY MEANS OF A GAS SENSOR"; (ii) the commonly assigned, copending U.S. application Ser. No. 06/590,230, filed Mar. 16, 1984, entitled "GAS DETECTION DEVICE HAVING A SENSOR COMPRISING AT LEAST ONE METAL OXIDE"; (iii) the commonly assigned, copending U.S. application Ser. No. 06/635,881, filed July 30, 1984, entitled "DEVICE FOR DETECTING GASEOUS CONTAMINANTS IN AIR BY MEANS OF A GAS SENSOR INCLUDING A SENSOR ELEMENT AND METHOD OF PRODUCING SUCH SENSOR ELEMENT"; and (iv) the commonly assigned, copending U.S. application Ser. No. 06/640,125, filed Aug. 13, 1984, entitled "DEVICE FOR SELECTIVELY DETECTING THE COMPONENTS OF GAS MIXTURES CONTAINED IN AIR BY MEANS OF A GAS SENSOR".

BACKGROUND OF THE INVENTION

The present invention relates to a new and improved method of producing constituent materials for gas sensors essentially consisting of at least one metal oxide with at least one catalyst additive.

Such materials and methods for their preparation are known. It has already been known for a long time that n-type semiconductors consisting of metal oxides adsorb reducing or oxidizing gases at their surface as a result of which a change in the electrical resistance occurs. Certain catalysts have been added to the metal oxides in order to increase the sensitivity with respect to reducing or oxidizing gases. Thus, a method of producing a material for gas sensors is known, for example, from German Pat. No. 2,428,488, published Jan. 9, 1975, which material contains tin dioxide as a base material and platinum as a catalyst. Furthermore, palladium is considered therefor as a metal catalyst and copper (II) oxide or nickel (II) oxide are considered as metal oxide catalysts therefor.

According to the known methods the base material is solely doped by impregnating the metal oxide powder with a solution of a precious metal salt like, for example, hydrogen hexachloroplatinate or disodium tetrachloropalladiate or a solution of a copper or nickel salt like, for example, copper chloride or nickel nitrate and by subsequent drying and heating. During the drying operation the metal salt is deposited in the form of small crystals and the metal salt decomposes during heating as a result of which the precious metal platinum or palladium remains in metallic form while the copper or nickel remains in the form of the metal oxide. The metal or metal oxide grains generally have an average diameter in the range of 10 to 500 nm. The local distribution of the grains, however, is not homogeneous since during the drying of the solution high local concentration differences occur at the metal oxide powder.

Gas sensors which are produced from such metal oxide powder, therefore, have highly variable sensitivities which differ from one sensor to the other. Furthermore, this method has the disadvantage that the anions of the metal salt or metal complex like, for example, the chloride or nitrate ions are bonded to vacancies in the metal oxide and so uncontrollably affect the conductivity of the metal oxide powder. This, in turn, results in variations in the sensitivity of the individual sensors.

In order to at least partially diminish the last mentioned effect the metal oxides were heated to temperatures of at least 600° to 1000° C. during the preparation in order to expel the aforementioned anions. At such high temperatures, however, the metal oxides sinter with a large volume reduction and then only have a small porosity. The general sensitivity of the gas sensor is thereby highly reduced.

In a method of preparing gas sensors as known, for example, from U.S. Pat. No. 4,362,765, granted Dec. 7, 1982, a mixture of a metal with its oxide is evaporated at reduced pressure in an oxygen-containing atmosphere, whereby there is obtained a layer of particles having an average diameter in range of 1 to several 10 nm on an insulating material which is provided with electrodes. The material for gas sensors obtained according to this procedure, however, has only low mechanical strength. When, for example, palladium is intended to be added as a catalyst to the oxide material which, for example, consists of tin dioxide, the catalyst can not be homogeneously distributed therein but has to be deposited thereon in a number of separate layers.

The photochemical deposition of metals on metal oxide powders is described in U.S. Pat. No. 4,264,421, granted Apr. 28, 1981, and is used for the preparation of catalyst powders. Such method requires acetate ions and a reaction temperature of up to 60° C. for an effective metal deposition.

The method according to the invention which is further described hereinafter basically differs from the method as known from the aforementioned U.S. Pat. No. 4,264,421:

Instead of a metal oxide powder which is suspended in a solution, there is used according to the inventive method a colloidal solution of metal oxides, metal oxide hydrates or metal hydroxides which is mixed with a metal salt solution and then irradiated.

The photochemical reaction is conducted at room temperature or even below. It is thus prevented that the irradiated colloidal solution coagulates. The acetate ions required for an efficient photoreaction according to U.S. Pat. No. 4,264,421 cause the colloidal solutions to coagulate.

In order to accelerate the photochemical reaction, therefore, no acetate ions are added in the method according to the invention as described further hereinafter, but there are added alcohols, ketones or other reductants which do not generate ionic products during oxidation or do not change the hydrogen ion concentration in the solution to such an extent that the irradiated colloidal solution would coagulate.

Contrary to this U.S. Pat. No. 4,264,421 there is not present a suspension after the irradiation of the mixture with ultraviolet or visible light in the method according to the invention but a true colloidal solution. This solution can be processed via a solid in order to obtain large pieces of metal oxide gels. When starting from a metal oxide suspension as described in U.S. Pat. No. 4,264,421, pieces of gel cannot be obtained under any circumstances; however, gel pieces are required for the preparation of the present extremely sensitive gas sensors. The solution as mentioned hereinbefore also can be lyophilized which yields the solid in the form of a fine powder. This powder consists of colloidal particles of the irradiated solution which have a much smaller diameter than the metal oxide grains utilized according to U.S. Pat. No. 4,264,421. Only when the herein described extremely small metal oxide particles are used, can there be ultimately produced the herein described gas sensors which are unique in their quality.

Further and again contrary to U.S. Pat. No. 4,264,421 the mixtures do not turn colorless during irradiation with light, but generally turn into a deep black color. The reason therefor is that the deposited metal is extremely finely distributed and is extremely finely deposited upon the colloidal metal oxide particles.

SUMMARY OF THE INVENTION

Therefore, with the foregoing in mind it is primary object of the present invention to provide a new and improved method of producing constituent materials for gas sensors essentially consisting of at least one metal oxide with at least one catalyst additive, which eliminates the disadvantages of hitherto used materials for gas sensors and particularly permits the production of gas sensors of essentially uniform sensitivity.

Another and more specific object of the present invention is to provide a new and improved method of producing constituent materials for gas sensors essentially consisting of at least one metal oxide with at least one catalyst additive which eliminates the differences in the conductivity of the metal oxide gas sensors due to the deposition of anions at metal oxide vacancies.

Still a further significant object of the present invention is directed to a new and improved method of producing constituent materials for gas sensors essentially consisting of at least one metal oxide with at least one catalyst additive which avoids or reduces heating during the preparation of the metal oxide materials to such an extent that the reduction in sensitivity due to the decrease in porosity during drying is prevented.

Another, still important object of the present invention is directed to a new and improved method of producing constituent materials for gas sensors essentially consisting of at least one metal oxide with at least one catalyst additive which yields gas sensor materials of increased general sensitivity which can be operated at room temperature or at a slightly increased temperature thereabove in order to reduce the current consumption in gas detecting installations.

Now in order to implement these and still further objects of the invention which will become more readily apparent as the description proceeds, the method of the present development is manifested by the features that, a colloidal solution A is prepared from an oxide or hydroxide of at least one metal selected from the groups Ib, IIa, IIb, IIIa, IIIb, IVa, IVb, Va, Vb, VIa, VIb, VIIb, VIII and the lanthanides and actinides of the periodic system. This solution A is mixed with a solution B of a salt or a complex compound of at least one metal selected from the group lanthanum, chromium, manganese, iron, cobalt, nickel, copper, ruthenium, iridium, palladium, platinum, rhodium, osmium, silver, gold, antimony, bismuth and thorium. In order to photochemically deposit the metal in finely distributed form on the metal oxide or metal hydroxide, the mixture is irradiated with electromagnetic radiation in the range of visible and ultraviolet light and there is obtained an irradiated solution C which is processed to yield a solid D without substantial change in the size of the colloidal metal oxide or metal hydroxide particles. Thereafter the solid D is dried at a temperature above the intended operating temperature of the gas sensor by a maximum of 700° C., particularly by a maximum of 500° C. and preferably by a maximum of 300° C.

According to a preferred embodiment of the inventive method the solid D is produced from the solution C by an extremely careful treatment like, for example, by partially evaporating the solvent or by lyophilizing the solution C. This solid D contains the colloidal metal oxide, metal hydroxide or metal oxide hydrate particles which initially have been produced in the solution A and which have been photochemically provided with metal in their original, insubstantially changed size which is in the range of 0.5 to 500 nm. This solid D is exposed in the further steps of the process which finally result in the finished gas sensor only to such temperatures which are higher than the later operating temperature of the gas sensor by a maximum of 700° C., particularly only by 500° C. and preferably by a maximum of 300° C. The solid D which, for example, may constitute a solvent impregnated piece of gel and contains a metal-charged metal oxide, metal hydroxide or metal oxide hydrate can be converted into a metal oxide xerogel by careful drying.

According to another variant of the method according to the invention there can also be obtained a highly porous metal oxide aerogel from the solution C by partially evaporating the solution C and thus transforming the same into a water-containing piece of gel which constitutes the solid D, by replacing the water with a non-aqueous solvent and by subjecting the piece of gel at a pressure which is supercritical with respect to the solvent to a temperature which is above the critical temperature of the solvent. After some time the pressure is then lowered to normal pressure and subsequently the temperature is lowered to room temperature.

According to a further variant of the method according to the invention a solution C which mainly contains non-aqueous solvents, is gelled and the solvents are then removed by drying at supercritical temperature and supercritical pressure as described hereinbefore in order to obtain a metal oxide aerogel.

An excellent gas sensor material is also obtained when according to a further variant of the inventive method the solution C which mainly contains non-aqueous solvents is partially evaporated and thereby converted into a solid D in the form of a metal oxide gel, metal hydroxide gel or metal oxide hydrate gel. This solid D is then dried under atmospheric pressure at a temperature which is above the later operating temperature of the gas sensor by a maximum of 700° C., particularly by a maximum of 500° C. and preferably by a maximum of 300° C. This gas sensor material which constitutes a metal oxide xerogel as well as the metal oxide xerogels or metal oxide aerogels obtained according to the other variants of the inventive method as described hereinbefore preferably have the shape of a circular plate or wafer having a thickness in the range of about 0.1 to 2 mm and a diameter up to some cm. Depending upon the mold into which the solution C is poured, there can be obtained, however, any desired shape of the solid D like, for example, cubes, quadrangled prisms, rods, tubes etc., with external dimensions of up to several centimeters or decimeters.

According to a preferred embodiment of the method according to the invention there is used a colloidal solution A of an oxide or hydroxide of at least one metal selected from the group beryllium, magnesium, calcium, strontium, barium, lanthanum, cerium, thorium, titanium, zirconium, vanadium, niobium, tantalum, chromium, molybdenum, tungsten, manganese, iron, cobalt, nickel, copper, silver, zinc, cadmium, aluminum, indium, silicon, germanium, tin, lead, antimony and bismuth as a starting material.

The solution A of the colloidal metal oxide, metal oxide hydrate or metal hydroxide required for carrying out the method according to the invention can be produced by hydrolysis of a metal salt which is effected by a change in the hydrogen ion concentration. The colloidal solution A can also be produced by hydrolyzing a metal alcoholate in a non-aqueous solvent by the addition of water. In a preferred method step there is added prior to the hydrolysis of the metal salt or the metal alcoholate a chelating agent; a product of further reduced particle size is thus obtained.

According to a further preferred embodiment of the inventive method a colloidal solution A of an oxide or hydroxide of at least one metal selected from the group magnesium, lanthanum, cerium, titanium, zirconium, vanadium, chromium, iron, cobalt, nickel, copper, zinc, aluminum, indium, antimony, tin is mixed with a solution B of the chloride, nitrate, sulphate, acetate, formate, acetylacetonate or salicylate of at least one of the metals selected from the group lanthanum, chromium, manganese, iron, cobalt, nickel, copper, ruthenium, iridium, palladium, platinum, rhodium, osmium, silver, gold, antimony, bismuth, thorium and then irradiated with light until at least 30%, particularly 60% and preferably at least 90% of the metal content of the solution B is deposited as a metal.

It is of particular advantage if a reducing agent is added to the mixture of the colloidal solution A of the metal oxide or metal hydroxide and the metal salt solution B, which reducing agent during the photoreaction causes a change in the hydrogen ion concentration by a maximum of 3 powers of ten. Preferably the photochemical metal deposition is conducted in the absence of aerial oxygen. This can be done in such a way that the solution is briefly evacuated prior to the irradiation and then maintained under a protective gas during the irradiation.

The aerial oxygen can also be removed from the mixture of the solutions A and B by flushing the mixture with a protective gas prior to the irradiation. This protective gas atmosphere is then maintained during the irradiation. Preferably nitrogen, helium, argon, neon, krypton, xenon, hydrogen or carbon dioxide is used as a protective gas. Preferably a chelating agent can be added to the mixture of the two solutions A and B prior to the photolysis. Chelating agents for this method step and also for preparing the solution A are preferably oxalic acid, tartaric acid, citric acid, acetylacetone, ethylenediamine tetraacetic acid, nitrilotriacetic acid or salicylic acid. According to a particularly preferred embodiment of the method according to the invention a chelating agent is selected which simultaneously acts as a reducing agent in the photoreaction.

Particularly favorable results are obtained when the solution A and/or the irradiated solution C are further purified by dialysis or electrodialysis.

According to a further preferred embodiment of the inventive method the irradiated solution C can be lyophilized. The powder thus obtained is applied either in a mixture with a sintering additive or as such to a substrate provided with electrodes and is sintered thereto. The powder thus obtained can also be heated for the removal of solvents and then can be pressed in order to form plates. For increasing the strength the lyophilized powder can be heated for solvent removal, pressed to form plates and then can be impregnated with a solution of an organic compound of silicon, titanium, aluminum or tin. Thereafter the powder is heated a second time for solvent removal.

From these plates which consist of pressed powder and possibly can still be mechanically reinforced by additives, as well as from the larger metal oxide xerogel bodies or plates or metal oxide aerogel bodies or plates as described hereinbefore there can now be severed smaller pieces of the desired shapes. If required, electrodes can also be applied thereto prior to this operation. These pieces have dimensions in the range of about 0.05 mm to several mm and are processed to yield gas sensors. It will be self-evident that it is also possible to initially produce these small pieces by pouring the solution C into appropriate small molds. In order to obtain the desired dimensions of these small pieces, however, the volume contraction during drying of the solution C will have to be considered. The powder obtained by lyophilizing the solution C can also be directly pressed to the desired small pieces.

According to the inventive method there is thus obtained a stable material for gas sensors which can be sawed, ground, polished, etched, provided with electrodes and can be processed in any other desired manner. The obtained material has a particle size smaller than 1 micrometer in the case of the metal oxide and smaller than 0.5 micrometer in the case of the catalyst additive. The material is extremely homogeneous so that the gas sensors produced therefrom have specific electrical conductivities and changes in the electrical conductivity and/or in the optical absorption under the action of reducing or oxidizing gases which are within extremely close tolerances.

Novel gas sensors can be produced from the constituent materials for gas sensors prepared in accordance with the method according to the invention, which novel gas sensors are vastly superior to conventional gas sensors. These novel gas sensors, for example, can be operated at room temperature or at temperatures which are only slightly above room temperature. The power consumption which in conventional gas sensors is in the range of about 1 watt can thereby be reduced to a value far below 100 mW per sensor.

Hitherto known gas sensors have an electrical conductivity which is proportional to the square root of the concentration of the gases to be detected. The gas sensor constituent materials produced according to the inventive method show, contrary thereto, within an extremely wide concentration range an electrical conductivity which is directly proportional to the concentration of the gases to be detected. This represents an enormous progress over the known gas sensors. Without specifically restricting the invention to this theory it is assumed that this result arises because the catalyst grains deposited on the metal oxide particles are considerably smaller and much more homogeneously distributed than in the hitherto known gas sensor materials. Such a fineness and homogeneity of the catalyst doping can not be achieved using the conventional methods. The metal oxide particles have an average diameter in the range of 5 to 10 nm as determined by X-ray diffraction measurements. This is lower by about one power of ten than the particle size of the hitherto known tin dioxide gas sensors which have a particle size in the range of 50 to 100 nm.

The invention will be better understood and objects other than those set forth above, will become apparent when consideration is given to the following detailed examples thereof.

GENERAL DESCRIPTION OF THE METHOD

In the hitherto known methods for producing catalyst-doped metal oxides the catalyst precursor usually was introduced into the metal oxide in the form of a solution of a metal salt or a metal complex compound. In the inventive method an entirely new principle is used for depositing the catalyst. The catalyst which constitutes a metal is photochemically generated already in a colloidal metal oxide, metal oxide hydrate or metal hydroxide solution.

For this purpose a colloidal solution A of an oxide, a hydroxide or an oxide hydrate of at least one metal selected from the groups Ib, IIa, IIb, IIIa, IIIb, IVa, IVb, Va, Vb, VIa, VIb, VIIb, VIII, the lanthanides and the actinides of the periodic system is prepared. This colloidal solution A may or may not contain a chelating agent and is mixed with a solution B which contains a salt or complex compound of at least one metal which forms the catalyst and which is selected from the group lanthanum, chromium, manganese, iron, cobalt, nickel, copper, ruthenium, iridium, palladium, platinum, rhodium, osmium, silver, gold, antimony, bismuth, and thorium. The mixture of the two solutions A and B is then irradiated with the radiation of a mercury vapor lamp at room temperature for several hours, whereby the catalyst metal is deposited on the colloidal metal oxide, metal hydroxide or metal oxide hydrate particles in an extremely finely distributed form. There is thus obtained a solution C which contains at least one catalyst metal-charged colloidal metal oxide, metal hydroxide or metal oxide hydrate. This photochemical catalyst metal deposition occurs at each irradiated metal oxide particle and the distribution of the catalyst metal is thus much finer than obtained by the hitherto known catalyst doping methods for producing materials for gas sensors. The concentration of the catalyst doping can be controlled by adjusting the mixing ratio of the two solutions A and B in a distinct manner or by adding solution A to the solution C after irradiation.

In order to accelerate the photochemical catalyst metal deposition the mixture of the solutions A and B additionally can contain reducing agents, for example, alcohols, ketones, etc. The mixture may contain either solely organic or solely inorganic solvents or a mixture of organic and inorganic solvents.

When the metal compounds in the solutions A and B contain inorganic or organic ions which can be removed from the obtained solid D only with difficulty, the solution C obtained after photolysis is freed from these ions by dialysis. If required, already the solution A can be subjected to dialysis. Instead of dialysis, electrodialysis may also be used for purification.

The thus obtained and, if desired, purified solution C ontains only colloidal metal oxide, metal oxide hydrate or metal hydroxide with catalyst metal deposited thereupon and is poured into a mold, partially evaporated therein and left to gel which yields a solid D which is finally dried by heating at a maximum heating rate of 100° C. per hour to a temperature which is not higher by a maximum of 700° C., particularly by a maximum of 500° C. and preferably by a maximum of 300° C. than the later operating temperature of the gas sensors. In this way a catalyst-doped metal oxide xerogel is obtained which has a predetermined porosity and particle size. Such material can be used as a constituent material for gas sensors of the type as described in the initially cross-referenced, copending U.S. application Ser. No. 06/635,881, filed July 30, 1984, entitled "DEVICE FOR DETECTING GASEOUS CONTAMINANTS IN AIR BY MEANS OF A GAS SENSOR INCLUDING A SENSOR ELEMENT AND METHOD OF PRODUCING SUCH SENSOR ELEMENT".

The solution C can also be lyophilized in order to produce the solid D, whereby an extremely fine powder is obtained which can be processed in the usual manner by pressing in molds in the absence or in the presence of a sintering additive and applying electrodes thereto or, respectively, by sintering onto a sensor element with electrodes applied thereto. In this manner there are also obtained sensors which react much more sensitively to the gases to be detected than the hitherto known gas sensors.

Depending on their electron affinity the catalyst metal is present in the powder obtained after the photochemical deposition and drying of the gel pieces or lyophilization in a more or less oxidized state.

During any of the herein described methods of further processing the irradiated solution C there is obtained a solid D which has not been subjected to any change in the particle size as compared to the particles contained in the irradiated solution C. The solid D constitutes a high-purity metal oxide, metal oxide hydrate or metal hydroxide gel. After drying, the material can be severed by cutting, sawing or the like to yield the constituent material of sensor elements for gas sensors which respond very sensitively to the presence of oxidizing or reducing gases in air by a change in their electrical and/or optical properties.

The invention will be still better understood by reference to the following examples.

EXAMPLE 1

5.8 g tin (IV) chloride ($SnCl_{4.5} H_2O$) were dissolved in 180 g of water and adjusted to a pH value of 7 by means of concentrated ammonia water at room temperature. The obtained precipitate of tin dioxide hydrate ($SnO_2.x H_2O$) is filtered, washed with water a number of times and subsequently vigorously stirred for several hours in a solution of 18 ml concentrated ammonia water in 55 ml water. The clear colloidal solution A of tin dioxide hydrate ($SnO_2.x H_2O$) thus obtained was dialysed for several days.

32 mg dihydrogen hexachloroplatinate ($H_2[PtCl_6].5 H_2O$) were dissolved in 46 ml water and the pH value was adjusted to 8.5 by adding soda. This solution B was added to the colloidal tin dioxide solution A obtained as hereinbefore. 7 ml isopropanol were added as a reducing agent in order to accelerate the photoreaction. The mixture thus obtained was irradiated in a nitrogen atmosphere for six hours with the light of a 200-W-mercury super pressure lamp at a temperature of 20°±3°. The deep black solution C thus obtained was dialysed for several days.

The solution thus obtained was poured into a mold and left to evaporate for several days preferably at room temperature. The thus obtained deep black gel plate containing platinum-doped tin dioxide was slowly heated to 300° C. within 9 hours, held at this temperature for 4 hours and then cooled again to room temperature. The thus obtained metal oxide xerogel plate was then ground and polished, whereafter electrodes could be applied to the sides of the plate by vacuum deposition. The plate was sawed into pieces having the dimensions $1 \times 1 \times 0.5$ mm$^3$. These pieces were applied to heatable substrates and optionally provided with electrodes, whereby gas sensors were obtained which reacted extremely sensitively to carbon monoxide at about 50° C. The electrical conductivity of these sensors is directly proportional to the carbon monoxide concentration, which proportionality up to now was not known with any of the commercially available gas sensors.

In a further experiment the solution B contained 36.4 mg palladium (II) chloride dissolved in 90 ml water which has been adjusted to a pH value of 9 by ammonia water. This solution B was added to the solution A and the mixture was processed as described hereinbefore to yield a gas sensor for very sensitively detecting n-butane.

In a still further experiment there was used a solution B composed of 20 ml of a solution of 38 mg copper nitrate (Cu [NO$_3$]$_2$.3H$_2$O)in 100 ml of water which was adjusted to a pH value of 10 by ammonia water. This solution B was added to the solution A and processed to a gas sensor as described hereinbefore which could very sensitively detect alcohol vapors.

EXAMPLE 2

100 ml of a colloidal tin dioxide solution A (SnO$_2$.xH$_2$O) were prepared as in Example 1. 52 mg rhodium (III) chloride (RhCl$_3$.3H$_2$O) were dissolved in 20 ml of water and adjusted to a pH value of 5 with ammonia water. This solution B was added to the colloidal tin dioxide solution A without addition of a reducing agent and the entire solution was irradiated for 24 hours as described in Example 1. The thus obtained deep black solution C was dialysed for several days, poured into a mold and then left to evaporate during several days preferably at room temperature. There was obtained a black gel plate formed of rhodium-doped tin dioxide which was heated within 5 hours to 320° C., left at this temperature for 1 hour and cooled again to room temperature. This metal oxide xerogel plate was ground, polished, provided with electrodes by screen printing and sawed into pieces having the dimensions $2 \times 1 \times 0.8$ mm$^3$. These pieces were processed to yield excellent gas sensors having an electric conductivity which linearly changes with hydrogen concentration.

EXAMPLE 3

50 ml of a colloidal solution C of tin dioxide containing 1 percent by weight of platinum were prepared analogously to Example 1. 2 ml of this solution C were mixed with 40 ml of a colloidal solution A of tin dioxide prepared in accordance with Example 1, poured into a mold and left to evaporate at room temperature for several days. There was obtained a transparent brown gel plate consisting of tin dioxide containing 0.05% by weight of platinum. The plate was heated to 550° C. within 2 hours, left at this temperature for 3 hours and then cooled again to room temperature. This plate was ground, polished, provided with highly reflecting electrodes and sawed into pieces having the dimensions $2 \times 2 \times 0.5$ mm$^3$. These gel pieces including the electrodes were mounted to heatable substrates and thus yielded gas sensors which could be used for optical as well as electrical detection of reducing or oxidizing gases.

EXAMPLE 4

100 ml of an aqueous suspension of titanium oxide hydrate are obtained by mixing a solution of 21 g of titanium tetrabutanolate [Ti(O(CH$_2$)$_3$ CH$_3$)$_4$] in 46.5 g methanol with 515 g water. The aqueous suspension was peptized by stirring with 10 ml of a solution of 12.7 g oxalic acid dihydrate in 125 g water. 10 ml of a solution B containing 89 mg palladium (II) acetate in 50 ml methanol were added to the clear solution A and the mixture was irradiated as in Example 1. There was obtained a brown solution C which was dialysed for several hours and then poured into a mold. This solution was partially evaporated at room temperature and left to gel and there was obtained a deep black gel plate consisting of palladium-doped titanium oxide. This plate was heated to 250° C. within 30 hours and then left to cool. This metal oxide xerogel plate thus obtained was ground, polished, provided with electrodes and then sawed into pieces having the dimensions $0.2 \times 0.2 \times 0.2$ mm$^3$. These pieces were processed to yield an excellent gas sensor for very sensitively detecting hydrogen.

EXAMPLE 5

3.1 g of titanium tetrabutanolate [Ti(O(CH$_2$)$_3$ CH$_3$)$_4$] were dissolved in 7 g of methanol and added to a solution of 1.4 g acetylacetone in 30.4 g water. Due to the chelating agent acetylacetone there was obtained an only moderately turbid solution A which was completely clarified by addition of 1.7 g concentrated formic acid. 5 ml of a solution B containing 30 mg of palladium (II) acetate in 20 ml methanol were added and the mixture was irradiated for several hours as in Example 4. The thus obtained dark brown solution was directly poured into a mold without dialysis, partially evaporated therein and left to gel, preferably at room temperature. The thus obtained black gel plate consisting of palladium-doped titanium dioxide was heated as in Example 4 to yield a metal oxide xerogel plate having a porosity of 59 percent by volume. From this plate there were cut pieces having the dimensions $1 \times 1 \times 0.8$ mm$^3$. Gas sensors produced therefrom very sensitively indicate carbon monoxide and hydrogen.

EXAMPLE 6

75 ml of a deep black solution C of colloidal tin dioxide charged with palladium were prepared as in Example 1 and dialysed. This solution was lyophilized and there was obtained a light brown-white, extremely fine powder. This powder was pressed to 1 mm thick plates having a diameter of 10 mm, electrodes were vapor deposited thereon and the plates were sawed to yield pieces having the dimensions $1 \times 1 \times 1$ mm$^3$. These pieces were processed to yield gas sensors means of which carbon monoxide and hydrogen can be detected already at room temperature. This Example shows that the particularly favorable operating properties of the gas sensor elements are due to the gas sensor constituent materials obtained by the method according to the invention. This is the case even when the constituent material of the sensor elements is pressed.

In a further experiment 110 ml of a colloidal titanium dioxide solution C containing titanium dioxide particles with palladium photochemically deposited thereupon were prepared as in Example 4. This solution was lyophilized and the thus obtained brownish powder was pressed to discs measuring 25 mm in diameter and 0.8 mm in thickness. These discs were impregnated with an alcoholic solution of orthosilicic acid ethyl ester [Si(OEt)$_4$] and dried for 4 hours at about 300° C. There were obtained thereby very stable, highly porous discs which were provided with electrodes by screen printing and then sawed to yield pieces with the dimensions 2×2×0.8 mm$^3$. The gas sensors prepared therefrom could very sensitively detect hydrogen and carbon monoxide.

In a variant the powder obtained by lyophilizing the irradiated solution C is heated prior to pressing the plates therefrom.

EXAMPLE 7

60 ml of a solution C of colloidal tin dioxide charged with extremely fine distributed rhodium were prepared as in Example 2. This solution was lyophilized and there was obtained a brown, extremely fine powder. This powder was stirred with a small amount of methanol to yield a slurry which was applied as a thin layer on an electrically insulating flat substrate consisting of aluminum oxide and provided with electrodes. The applied slurry was dried at about 50° C. and impregnated with a methanol solution of orthosilicic acid methylester [Si(OMe)$_4$] and subsequently dried for 4 hours at about 300° C. Silica was formed thereby which cemented the fine tin dioxide particles to each other and nevertheless yielded a porous layer. The sensor could be excellently used for the detection of carbon monoxide at 80° C.

Alternatively the dried powder is mixed with a sintering additive, the mixture is applied to the substrate and sintered thereto.

EXAMPLE 8

73 ml of a colloidal tin dioxide solution C containing extremely finely distributed palladium on tin dioxide particles having a diameter of a few nm were prepared as in Example 1 and lyophilized. The thus obtained fine powder was heated for 1 hour at 300° C. and pressed to yield cubes of the outer dimensions 2×2×2 mm$^3$ and having a central circular hole of 0.8 mm diameter. Two outer surfaces of such cube were each provided with a related electrode. This cube was used in a multiple gas sensor containing a number of analogous cubes consisting of tin dioxide and having a central hole but doped with other catalysts than palladium. The monoxide at operating temperature of 180° C. Further details palladium-doped tin dioxide cube is very sensitive to carbon thereof are described in the initially cross-referenced, copending U.S. application Ser. No. 06/635,881, filed July 30, 1984, entitled "DEVICE FOR DETECTING GASEOUS CONTAMINANTS IN AIR BY MEANS OF A GAS SENSOR INCLUDING A SENSOR ELEMENT AND METHOD OF PRODUCING SUCH SENSOR ELEMENT".

In a variant the plates which are obtained by heating and pressing the dried powder are further subjected to sintering.

EXAMPLE 9

44 g of an aqueous solution A containing 20 g per liter of colloidal tin dioxide were prepared as in Example 1. 18.7 mg of diammonium hexachlororuthenate and 17.4 mg of diammonium tetrachloroplatinate were dissolved in 30 ml water. This solution B was added to the colloidal tin dioxide solution A and the combined solutions were irradiated for 24 hours as in Example 1. There was obtained a deep brown-black solution C which was dialysed for several days and then poured into a mold. The solution was partially evaporated at room temperature and left to gel. There was thus obtained a black plate of a platinum and ruthenium-doped tin dioxide gel which was heated to 525° C. within 30 hours and then cooled again. This plate which now consists of a tin dioxide xerogel doped with platinum and ruthenium and their oxides, was ground, polished, provided with electrodes by screen printing and cut to pieces having the dimensions 1×1×0.2 mm$^3$. These pieces were processed to yield gas sensors which extremely sensitively indicate hydrogen and carbon monoxide at an operating temperature of 186° C.

EXAMPLE 10

A colloidal solution C of palladium-doped titanium dioxide was produced as in Example 5 and diluted with such an amount of methanol that the water content was only 50% by volume. This solution was poured into a mold and then left to evaporate and gel for several days, preferably at room temperature. The thus obtained gel plate was placed into methanol which was renewed several times and then heated for at least half an hour together with methanol under pressure to such an extent that the critical pressure and the critical temperature of methanol were exceeded. The pressure was then lowered to normal pressure and subsequently the temperature was brought to room temperature. The thus obtained metal oxide aerogel was ground, polished, provided with electrodes and sawed to pieces by means of which hydrogen could be very sensitively detected at about 350° C.

EXAMPLE 11

4.2 g titanium tetrabutanolate [Ti(O(CH$_2$)$_3$ CH$_3$)$_4$] and 1.4 g acetylacetone as a chelating agent were dissolved in 8.9 g methanol and 1 ml water was added with stirring. 3.2 g of a solution B containing 25 mg palladium (II) acetate in 13 ml of methanol were added to the thus obtained colloidal titanium dioxide solution A and the mixture was irradiated for 9 hours as in Example 1. This solution C was poured into a mold without dialysis, partially evaporated therein, preferably at room temperature and gelled thereby after several days. The thus obtained gel plate was then heated to 300° C. within 10 hours, maintained at this temperature for 4 hours and cooled again to room temperature. The metal oxide xerogel plate thus obtained was ground, polished, provided with electrodes and sawed into pieces of the size 1×1×1 mm$^3$ which were processed to yield gas sensors by means of which hydrogen could very sensitively be detected at about 300° C.

EXAMPLE 12

A colloidal titanium dioxide solution A in methanol was produced analogous to Example 11 and a methanolic palladium (II) acetate solution B was added thereto. The palladium was deposited on the titanium dioxide colloid particles by UV-irradiation as in Example 1. The thus obtained solution C was poured into a mold, partially evaporated therein, preferably at room temperature and thus gelled after several days. The thus obtained gel plate containing the organic solvent methanol was heated together with methanol under pressure such that the critical pressure and the critical temperature of methanol were exceeded. The pressure was then lowered to normal pressure and subsequently the temperature was brought to room temperature. The thus obtained plate of titanium dioxide aerogel was ground, polished, provided with electrodes, and sawed to yield pieces. These pieces were processed to yield gas sensors by means of which hydrogen, methane and carbon monoxide could be very sensitively detected at a temperature of about 280° C.

While there are described present preferred embodiments of the invention, it is to be distinctly understood that the invention is not limited thereto, but may be otherwise variously embodied and practiced within the scope of the following claims. ACCORDINGLY,

What I claim is:

1. A method of producing constituent materials for gas sensors comprising at least one metal oxide with at least one catalyst additive, comprising the steps of:
   preparing a colloidal solution A of colloidal particles of any one of at least an oxide, oxide hydrate or hydroxide of at least one metal selected from the groups Ib, IIa, IIb, IIIa, IIIb, IVa, IVb, Va, Vb, VIa, VIb, VIIb, VIII, the lanthanides, and the actinides of the periodic system;
   preparing a solution B of a salt or complex compound of at least one metal selected from the group consisting of: lanthanum, chromium, manganese, iron, cobalt, nickel, copper, ruthenium, iridium, palladium, platinum, rhodium, osmium, silver, gold, antimony, bismuth, and thorium;
   mixing said colloidal solution A and said solution B;
   irradiating the mixture of the colloidal solution A and the solution B with electromagnetic radiation in order to deposit the metal contained in solution B in finely distributed form on the colloidal particles of said oxide, oxide hydrate or hydroxide contained in colloidal solution A and to obtain an irradiated solution C; and
   processing said irradiated solution C in order to obtain a solid D without a substantial change in the size of the colloidal particles formed by said oxide, oxide hydrate or hydroxide.

2. The method as defined in claim 1, wherein:
   the step of irradiating the mixture of the colloidal solution A and the solution B with electromagnetic radiation includes the step of irradiating the mixture with electromagnetic radiation in the ultraviolet region of the spectrum.

3. The method as defined in claim 1, wherein:
   the step of irradiating the mixture of the colloidal solution A and the solution B with electromagnetic radiation includes the step of irradiating the mixture with electromagnetic radiation of the visible and ultraviolet region of the spectrum.

4. The method as defined in claim 1, further including the step of:
   drying said solid D at a temperature above a predetermined operating temperature of the gas sensor made of said solid as the constituent material thereof.

5. The method as defined in claim 4, wherein:
   the step of drying said solid D includes the step of heating the same to a maximum temperature of 700° C. above said predetermined operating temperature of said gas sensor.

6. The method as defined in claim 4, wherein:
   the step of drying said solid D includes the step of heating the same to a maximum temperature of 500° C. above said predetermined operating temperature of said gas sensors.

7. The method as defined in claim 4, wherein:
   the step of drying said solid D includes the step of heating the same to a maximum temperature of 300° C. above said predetermined operating temperature of said gas sensor.

8. The method as defined in claim 1, wherein:
   the step of preparing the colloidal solution A includes the step of preparing a colloidal solution A which contains any one of at least an oxide, oxide hydrate or hydroxide of at least one metal selected from the group beryllium, magnesium, calcium, strontium, barium, lanthanum, cerium, thorium, titanium, zirconium, vanadium, niobium, tantalum, chromium, molybdenum, tungsten, manganese, iron, cobalt, nickel, copper, silver, zinc, cadmium, aluminum, indium, silicon, germanium, tin, lead, antimony, and bismuth.

9. The method as defined in claim 1, wherein:
   the step of preparing said colloidal solution A includes the steps of:
   preparing an aqueous solution of a salt of said at least one metal; and
   hydrolyzing the at least one metal salt in said aqueous solution by changing the hydrogen ion concentration therein in order to prepare said colloidal solution A.

10. The method as defined in claim 9, further including the step of:
    adding a chelating agent to said aqueous solution of said at least one metal salt prior to hydrolyzing the same.

11. The method as defined in claim 1, wherein:
    the step of preparing said colloidal solutiion A includes the steps of:
    preparing a solution of an alcoholate of said at least one metal; and
    adding water to the metal alcoholate solution in order to hydrolyze said at least one metal alcoholate and to prepare said colloidal solution A.

12. The method as defined in claim 11, further including the step of:
    adding a chelating agent to said at least one metal alcoholate solution prior to hydrolyzing the same.

13. The method as defined in claim 1, wherein:
    the step of preparing said colloidal solution A includes the step of preparing a colloidal solution of any one of at least an oxide, oxide hydrate or hydroxide of at least one metal selected from the group: magnesium, lanthanum, cerium, titanium, zirconium, vanadium, chromium, iron, cobalt, nickel, copper, zinc, aluminum, indium, and tin; and
    the step of preparing the solution B includes the step of preparing a solution of a chloride, nitrate, sulphate, acetate, formiate, acetylacetonate, or salicylate of at least one metal selected from the group: lanthanum, chromium, manganese, iron, cobalt, nickel, copper, ruthenium, iridium, palladium, platinum, rhodium, osmium, silver, gold, antimony, bismuth, and thorium.

14. The method as defined in claim 1, wherein:
    the step of irradiating the mixture of the colloidal solution A and the solution B includes the step of irradiating said mixture at an intensity and for a duration resulting in a reduction of the metal salt or complex compound contained in solution B to the metallic state in the range of at least 30 to at least 90 percent.

15. The method as defined in claim 1, further including the steps of:
adding a reductant to the mixture obtained by mixing said solutions A and B; and
selecting a reductant which does not cause an increase in the hydrogen ion concentration by more than 3 powers of 10 as a result of the irradiation of the mixture during the metal deposition.

16. The method as defined in claim 14, further including the steps of:
adding a reductant to the mixture obtained by mixing said solutions A and B; and
selecting a reductant which does not cause an increase in the hydrogen ion concentration by more than 3 powers of 10 as a result of the irradiation of the mixture during the metal deposition.

17. The method as defined in claim 1, further including the step of:
adding a chelating agent to the mixture of said solutions A and B prior to irradiating said mixture.

18. The method as defined in claim 14, further including the step of:
adding a chelating agent to the mixture of said solutions A and B prior to irradiating said mixture.

19. The method as defined in claim 17, further including the step of:
selecting the chelating agent from the group of chelating agents which act as reductants during the irradiation for depositing said metal on said metal oxide, oxide hydrate or hydroxide.

20. The method as defined in claim 18, further including the step of:
selecting the chelating agent from the group of chelating agents which act as reductants during the irradiation for depositing said metal on said metal oxide, oxide hydrate or hydroxide.

21. The method as defined in claim 20, further including the step of:
selecting said chelating agent from at least one of the group consisting of: oxalic acid, tartaric acid, citric acid, acetylacetone, ethylenediaminetetraacetic acid, nitrilotriacetic acid, and salicyic acid.

22. The method as defined in claim 19, further including the step of:
selecting said chelating agent from at least one of the group consisting of: oxalic acid, tartaric acid, citric acid, acetylacetone, ethylenediaminetetraacetic acid, nitrilotriacetic acid, and salicylic acid.

23. The method as defined in claim 17, further including the step of:
selecting said chelating agent from at least one of the group consisting of: oxalic acid, tartaric acid, citric acid, acetylacetone, ethylenediaminetetraacetic acid, nitrilotriacetic acid, and salicylic acid.

24. The method as defined in claim 12, further including the step of:
selecting said chelating agent from at least one of the group consisting of: oxalic acid, tartaric acid, citric acid, acetylacetone, ethylenediaminetetraacetic acid, nitrilotriacetic acid, and salicylic acid.

25. The method as defined in claim 10, further including the step of:
selecting said chelating agent from at least one of the group consisting of: oxalic acid, tartaric acid, citric acid, acetylacetone, ethylenediaminetetraacetic acid, nitrilotriacetic acid, and salicylic acid.

26. The method as defined in claim 1, wherein:
the step of irradiating said mixture of the colloidal solution A and the solution B in order to deposit the metal includes the step of substantially conducting the irradiation in the presence of a protective gas; and
selecting said protective from the group essentially consisting of: nitrogen, helium, argon, neon, krypton, xenon, hydrogen, carbon dioxide.

27. The method as defined in claim 14, wherein:
the step of irradiating said mixture of the colloidal solution A and the solution B in order to deposit the metal includes the step of substantially conducting the irradiation in the presence of a protective gas; and
selecting said protective from the group essentially consisting of: nitrogen, helium, argon, neon, krypton, xenon, hydrogen, carbon dioxide.

28. The method as defined in claim 1, further including the step of:
purifying the prepared colloidal solution A by dialysis.

29. The method as defined in claim 1, further including the step of:
purifying the prepared colloidal solution A by electrodialysis.

30. The method as defined in claim 1, further including the step of:
purifying said irradiated solution C by dialysis.

31. The method as defined in claim 1, further including the step of:
purifying said irradiated solution C by electrodialysis.

32. The method as defined in claim 1, further including the steps of:
purifying the prepared colloidal solution A by dialysis; and
purifying said irradiated solution C by dialysis.

33. The method as defined in claim 1, further including the steps of:
purifying the prepared colloidal solution A by electrodialysis; and
purifying said irradiated solution C by electrodialysis.

34. The method as defined in claim 1, wherein:
the step of processing said irradiated solution C includes the steps of:
lyophilizing said irradiated solution C to obtain a powder;
drying the powder obtained by lyophilizing said irradiated solution C; and
providing a substrate with electrodes and applying the dried powder to said substrate.

35. The method as defined in claim 34, further including the steps of:
mixing said dried powder with a sintering additive;
applying the mixture thus obtained to said substrate; and
sintering said mixture to said substrate.

36. The method as defined in claim 1, wherein:
the step of processing said irradiated solution C includes the steps of:
lyophilizing said irradiated solution C in order to yield a powder;
heating said powder thus obtained in order to remove solvent therefrom; and
pressing the powder after heating in order to form plates therefrom.

37. The method as defined in claim 36, further including the step of: sintering said plates.

38. The method as defined in claim 1, wherein:
the step of processing said irradiated solution C includes the steps of:
lyophilizing said irradiated solution C in order to yield a powder;
pressing said powder in order to form plates therefrom;
impregnating said plates with a solution of an organic compound of at least one of the elements selected from the group consisting of: silicon, titanium, aluminum, and tin; and
heating said impregnated plates in order to remove solvent therefrom.

39. The method as defined in claim 38, further including the step of:
heating said powder obtained by lyophilizing said irradiated solution C for solvent removal prior to pressing the same into plates.

40. The method as defined in claim 1, wherein:
the step of processing said irradiated solution C includes the steps of:
pouring said irradiated solution C into a mold and evaporating the same therein at room temperature for several days in order to form a solid gel D essentially consisting of a high-purity metal oxide gel, metal oxide hydrate gel or metal hydroxide gel; and
in order to yield a metal oxide xerogel having a predetermined porosity and grain size, heating said solid gel D under normal pressure and at a maximum heating rate of 100° C. per hour to a predetermined temperature higher than a predetermined operating temperature of the gas sensor produced therefrom and subsequently cooling the product to room temperature.

41. The method as defined in claim 40, wherein:
the step of heating said solid gel D includes the step of heating the same to a maximum temperature of 700° C. above said predetermined operating temperature of said gas sensor.

42. The method as defined in claim 40, wherein:
the step of heating said solid gel D includes the step of heating the same to a maximum temperature of 500° C. above said predetermined operating temperature of said gas sensor.

43. The method as defined in claim 40, wherein:
the step of heating said solid gel D includes the step of heating the same to a maximum temperature of 300° C. above said predetermined operating temperature of said gas sensor.

44. The method as defined in claim 1, wherein:
the step of processing said irradiated solution C includes the steps of:
pouring said irradiated solution C into a mold and evaporating the same therein at room temperature for several days in order to form a solid gel D essentially consisting of a high-purity metal oxide gel, metal oxide hydrate gel or metal hydroxide gel; and
converting said solid gel D into a metal oxide aerogel having a predetermined porosity and grain size by:
repeatedly adding an organic solvent to said solid D at normal pressure and at room temperature for several weeks in order to obtain a solid containing said organic solvent;
subjecting for at least half an hour the thus obtained solid containing said organic solvent to a pressure and to a temperature which are supercritical with respect to said solvent; and
lowering the pressure to normal pressure and changing the temperature to room temperature.

45. The method as defined in claim 1, wherein:
the step of processing said irradiated solution C includes the steps of:
pouring said irradiated solution C which is made up of an organic solvent into a mold and evaporating the same therein at room temperature for several days in order to form a solid gel D essentially consisting of a high-purity metal oxide gel, metal oxide hydrate gel or metal hydroxide gel containing said organic solvent; and
in order to obtain from said solid D a metal oxide aerogel having a predetermined porosity and grain size, subjecting for at least half an hour the thus obtained solid gel D to a pressure and to a temperature which are supercritical with respect to said solvent, lowering the pressure to normal pressure and changing the temperature to room temperature.

46. The method as defined in claim 1, wherein:
the step of processing said irradiated solution C includes the steps of:
pouring said irradiated solution C which is made up of an organic solvent into a mold and evaporating the same therein at room temperature for several days in order to form a solid gel D essentially consisting of a high-purity metal oxide gel, metal oxide hydrate gel or metal hydroxide gel containing said organic solvent; and
in order to yield a metal oxide xerogel having a predetermined porosity and grain size, heating said solid gel D under normal pressure and at a maximum heating rate of 100° C. per hour to a predetermined temperature higher than a predetermined operating temperature of the gas sensor produced therefrom and subsequently cooling the product to room temperature.

47. The method as defined in claim 46, wherein:
the step of heating said solid gel D includes the step of heating the same to a maximum temperature of 700° C. above said predetermined operating temperature of said gas sensor.

48. The method as defined in claim 46, wherein:
the step of heating said solid gel D includes the step of heating the same to a maximum temperature of 500° C. above said predetermined operating temperature of said gas sensor.

49. The method as defined in claim 46, wherein:
the step of heating said solid gel D includes the step of heating the same to a maximum temperature of 300° C. above said predetermined operating temperature of said gas sensor.

50. The method as defined in claim 40, further including the step of:
severing a predetermined shaped sensor element for a gas sensor from said metal oxide xerogel.

51. The method as defined in claim 44, further including the step of:
severing a predetermined shaped sensor element for a gas sensor from said metal oxide aerogel.

52. The method as defined in claim 45, further including the step of:
severing a predetermined shaped sensor element for a gas sensor from said metal oxide aerogel.

53. The method as defined in claim 46, further including the step of:

severing a predetermined shaped sensor element for a gas sensor from said metal oxide xerogel.

54. The method as defined in claim 36, further including the step of:

severing a predetermined shaped sensor element for a gas sensor from said pressed plates.

55. The method as defined in claim 38, further including the step of:

severing a predetermined shaped sensor element for a gas sensor from said pressed, impregnated and heated plates.

* * * * *

UNITED STATES PATENT AND TRADEMARK OFFICE
CERTIFICATE OF CORRECTION

PATENT NO. : 4,579,751
DATED : April 1, 1986
INVENTOR(S) : MARTIN FORSTER

It is certified that error appears in the above—identified patent and that said Letters Patent is hereby corrected as shown below:

Column 11, line 49, delete "The monoxide at"

Column 11, delete lines 50, 51, 52 and 53 in their entirety

Column 11, line 49, after "palladium." insert --The palladium-doped tin dioxide cube is very sensitive to carbon monoxide at an operating temperature of 180°C. Further details thereof are described in the initially cross-referenced, copending U.S. application Serial No.--

Column 14, line 35, delete "solutiion" and insert --solution--

Signed and Sealed this

Fifth Day of August 1986

[SEAL]

*Attest:*

DONALD J. QUIGG

*Attesting Officer*  *Commissioner of Patents and Trademarks*